(12) United States Patent
Simpson et al.

(10) Patent No.: US 6,923,539 B2
(45) Date of Patent: Aug. 2, 2005

(54) ASPHERIC LENSES

(75) Inventors: Michael J. Simpson, Arlington, TX (US); Daniel R. Carson, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 256 days.

(21) Appl. No.: 10/437,687

(22) Filed: May 12, 2003

(65) Prior Publication Data

US 2004/0230299 A1 Nov. 18, 2004

(51) Int. Cl.[7] ................................................ G02C 7/04
(52) U.S. Cl. .............................. 351/160 R; 351/160 H
(58) Field of Search .................... 351/160 R, 160 H, 351/161, 162

(56) References Cited

U.S. PATENT DOCUMENTS

| | | |
|---|---|---|
| 4,279,480 A | 7/1981 | Bettiol et al. |
| 4,504,982 A | 3/1985 | Burk |
| 4,640,595 A | 2/1987 | Volk |
| 5,173,723 A | 12/1992 | Volk |
| 5,428,412 A | 6/1995 | Stoyan |
| 5,436,678 A | 7/1995 | Carroll |
| 5,502,518 A | 3/1996 | Lieberman |
| 5,570,142 A | 10/1996 | Lieberman |
| 5,715,031 A | 2/1998 | Roffman et al. |
| 5,796,462 A | 8/1998 | Roffman et al. |
| 5,835,186 A | 11/1998 | Copeland et al. |
| 5,835,187 A | 11/1998 | Martin |
| 5,922,821 A | 7/1999 | Lebouef et al. |
| 6,353,069 B1 | 3/2002 | Freeman |
| 6,802,605 B2 * | 10/2004 | Cox et al. ............... 351/160 R |

OTHER PUBLICATIONS

"A Significant Breakthrough in Intraocular Lens Design," Opthalmology Times, vol. 27 Supp. 2 (Jul. 15, 2002), 1–11.
Atchison, David A. "Design of aspheric intraocular lenses," Opthal.Physiol. Opt., 1991, vol. 11, Apr.

* cited by examiner

Primary Examiner—Scott J. Sugarman
(74) Attorney, Agent, or Firm—Jeffrey S. Schira (57) ABSTRACT

The present invention provides monofocal ophthalmic lenses that exhibit extended depth of field while providing sufficient contrast for resolution of an image over a selected range of defocus distances. In some embodiments, a lens of the invention can include a refractive surface having controlled surface modulations relative to a base profile. The surface modulations are designed to extend a depth of field of the lens such that a single image can be resolved, albeit with somewhat less contrast, over a range of distances greater than the focal region of a conventional lens. The ophthalmic lenses of the invention can be employed in various vision correction applications, including, but not limited to, intraocular lenses, contact lenses, instrastromal implants and other refractive devices.

18 Claims, 7 Drawing Sheets

FIG. 9
VISUAL ACUITY vs. DEFOCUS

FIG. 10

ASPHERIC LENSES

BACKGROUND OF THE INVENTION

The present invention relates generally to ophthalmic lenses, and more particularly to ophthalmic lenses that provide an enhanced depth of field.

A variety of ophthalmic lenses are employed for correcting visual disorders, such as cataract, myopia, hyperopia or astigmatism. For example, an intra-ocular lens (IOL) can be implanted in a patient's eye during cataract surgery to compensate for the lost optical power of the removed lens. In many cases, however, the implanted lens may not provide the best focus at the targeted object distance. Some studies have reported that refractive errors as large as 0.5 Diopters can occur in about fifty percent of patients who receive IOLs. Such errors can be caused, for example, by inherent variability associated with calculation methods utilized to choose an IOL's refractive power, inaccuracies in preoperative biometry data, or variations in the IOL's axial placement, tilt or decentration.

A variety of ophthalmic monofocal, bifocal, and multifocal lenses are known in the art that can be employed, among other applications, to ameliorate the above problems associated with IOLs. Examples of such ophthalmic lenses can include zonal refractive lenses, in which different zones of the lens exhibit different optical powers, and diffractive lenses, in which different diffraction orders are utilized to obtain multi-focal behavior. Such conventional ophthalmic lenses suffer from a number of shortcomings. For example, errors in axial placement of conventional monofocal lenses can significantly degrade their performance.

Accordingly, there is a need for improved monofocal ophthalmic lenses for visual correction that are less prone to refractive errors due to design or positioning factors.

SUMMARY OF THE INVENTION

The present invention provides monofocal ophthalmic lenses that exhibit extended depth of field while providing sufficient contrast for resolution of an image over a selected range of defocus distances. Methods of correcting refractive errors or otherwise enhancing vision over a range of such distances are disclosed, as well as methods of manufacturing the lenses of the present invention. The extended depth of field is achieved by introducing a minor modulation to the base curve of one or more lens elements such that the eye resolves a single image over a range of distances greater than the focal region of a conventional lens, with a modest level of contrast reduction.

The ophthalmic lenses of the present invention can be used in various vision correction applications including, but not limited to, intraocular lenses (IOLs) that can be used for both pseudophakic and phakic applications. The invention can also be useful in connection with contact lenses, intrastromal implants and other refractive devices.

More particularly, in one aspect, the invention provides a monofocal ophthalmic lens for vision correction that includes a lens optic that provides a nominal diopter power. The lens optic is further characterized by at least one refractive surface having a base curvature and a pattern of surface deviations superimposed on the base curvature so as to modulate the profile of the refractive surface in a range of about −0.5 microns to about +0.5 microns about the base curvature. The surface modulations are designed so as to enhance the depth of field of the lens by at least about 40%, and preferably by at least about 50% percent, and more preferably by at least about 60%, relative to a lens having the same lens optic and the same refractive surface, but without the surface modulation.

The terms "depth of field" and "depth of focus" in the context of a lens are well known and readily understood by those skilled in the art as referring to the distances in the object and image spaces over which an acceptable image can be resolved. To the extent that a quantitative measurement is necessary to describe the present invention, the term "depth of field" or "depth of focus" as used herein, more specifically can be measured by an amount of defocus associated with the lens at which a through-focus modulation transfer function (MTF) of the lens measured with a 3 mm aperture and green light, e.g., light having a wavelength of about 550 nm, exhibits a contrast of at least about 15% at a spatial frequency equal to about one-third of the diffraction limited spatial frequency associated with that lens. Other definitions can also be applied and it should be clear that depth of field is influenced by many factors including, for example, aperture size, chromatic content of the light from the image, and base power of the lens itself. Nonetheless, the MTF test, described above and explained in more detail below, is presented as a straightforward test of applicant's invention.

In a related aspect, the surface modulations superimposed on the refractive surface of the lens can be characterized by a continuously varying curve. A variety of different continuously varying curves can be employed to define a pattern of surface deviations for a lens according to the teachings of the invention. For example, the pattern of surface deviations can be defined in accordance with a sinusoidal-type curve.

In another aspect, the base curvature of the refractive surface and the pattern of surface deviations superimposed on the refractive surface can be selected to be radially symmetric. That is, all points on the surface having the same radial distance (r) from an optical axis of the lens exhibit substantially similar base curvature and deviations from the base curvature. In other words, the topography of the refractive surface modulated by the pattern of surface deviations can be radially symmetric about the optical axis of the lens.

An IOL according to the teachings of the invention can have any nominal power suited for a particular application. In one embodiment, particularly suited for IOL applications for cataract patients, an ophthalmic lens of the invention can exhibit a nominal power in a range of about 17 to about 25 Diopters. In other applications, phakic lenses having negative nominal power can be formed according to the teachings of the invention.

In another aspect, the invention provides a monofocal ophthalmic lens for vision correction that exhibits an extended depth of field, and includes a lens optic with a refractive surface having a base profile that is modulated by a pattern of surface deviations in accordance with the following relation:

$$Z(r)=A(r)\cos(B(r)r^2)$$

wherein $Z(r)$ denotes a surface deviation associated with the refractive surface at a radial distance r from the optical axis of the lens, and $A(r)$ and $B(r)$ are functions of radial distance r. The functions A and B are selected so as to enhance the depth of field of the lens by at least about 40%, and more preferably by at least about 50%, relative to a lens having the same lens optic, but without the surface deviations.

The parameters A and B can assume a variety of functional forms. In some embodiments, A and B are constants that do not vary with the radial distance (r) while in other embodiments, A and B assume functional forms that vary continuously with the radial distance (r). For example, either A or B, or both, can be characterized by a polynomial function of rank n defined in accordance with the following relations:

$$A(r) = a + a_1 r + a_2 r^2 + \ldots + a_n r^n, \text{ and}$$

$$B(r) = b_0 + b_1 r + b_2 r^2 + \ldots + b_n r^n$$

wherein n can be less than about 20, and the parameters $a_0$–$a_n$, and $b_0$–$b_n$ are selected such that the defined pattern of surface deviations would provide a depth of field that is enhanced by at least about 40%, and more preferably by at least about 50%, relative to a similar lens that is devoid of the surface deviations.

In a related aspect, the functional parameter A is selected to have a maximum value in a range of about 0.05 microns to about 0.5 microns, and more preferably in a range of about 0.15 microns to about 0.45 microns. Further, the functional parameter B is selected to have a minimum value in a range of about $$\frac{2\pi}{5}$$

to about $2\pi$ (microns)$^{-2}$. More generally, A can have a maximum value in a range of about $$\frac{1}{100 * (n_2 - n_1)}$$

to about $$\frac{1}{10 * (n_2 - n_1)}$$

microns, wherein $n_2$ denotes an index of refraction of the lens body and $n_1$ denotes a refraction index of the environment in which the lens is disposed.

In further aspects, the lens body of a lens according to the teachings of the invention can be formed of any suitable biocompatible material. For example, the lens body can be formed of a soft acrylic, hydrogel, or silicone material. For example, the lens body can be formed of polymethyl methacrylate (PMMA). In some embodiments, especially when a foldable IOL lens is desired, the lens can be formed of a copolymer of acrylate and methacrylate. For illustrative examples of such copolymer compositions, see for example, U.S. Pat. No. 5,922,821 entitled "Ophthalmic Lens Polymers" issued to Lebouef et al. on Jul. 13, 1999 and U.S. Pat. No. 6,353,069 entitled "High Refractive Index Ophthalmic Device Materials" issued to Freeman et al. on Mar. 5, 2002, the teachings of both of which are hereby incorporated by reference.

In other aspects, the invention provides methods for forming a lens according to the teachings of the invention. For example, in one such method, in an initial step, a circularly symmetric base profile is selected for at least one refractive surface of the lens. Subsequently, a pattern of surface deviations from the base profile is defined, and is applied to the base profile so as to define a continuously varying topography for the refractive surface. The pattern of surface deviations is selected to be circularly symmetric and continuously varying across the refractive surface so as to effect enhancement of the depth of field of the lens relative to a similar lens that is devoid of the surface deviations.

In a related aspect, the pattern of surface deviations can be defined by selecting a plurality of locations, each positioned at a selected radial distance from the optical axis of the lens, on the base curve. Subsequently, for each of these locations, a position deviated from the location in a direction perpendicular to the radial direction is defined. Further, for each deviated position, a slope is defined. A spline fitting procedure is utilized to define a continuously varying surface that extends through the deviated positions and exhibits the slopes defined at these positions. Subsequently, an enhancement of a depth of field of the lens, if any, is determined by employing the continuously varying surface as a profile of the refractive surface. The deviated positions and/or their associated slopes are then iteratively adjusted such that the depth of field is enhanced by at least about 40%, and preferably by at least about 50%, and more preferably by at least about 60%.

Further understanding of the invention can be obtained by reference to the following detailed description and the associated drawings, which are described briefly below.

DETAILED DESCRIPTION

The present invention provides an ophthalmic lens that exhibits an extended depth of field by a controlled modulation of the surface topography of at least one refractive surface of the lens so as to extend the depth of field of the lens by about at least 40%, and more preferably by at least about 50%, relative to a similar lens that is devoid of the surface modulations. A lens of the invention can thus correct refractive errors or otherwise enhance vision by providing sufficient contrast for resolution of an image over a selected range of defocus distances that are commensurate with an enhanced depth of field exhibited by the lens.

Figure 1:
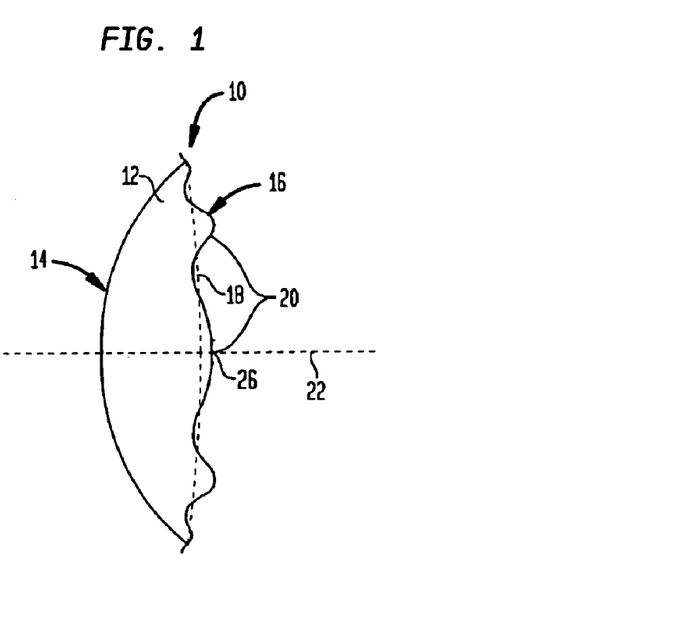
FIG. 1 schematically depicts a lens according to the teachings of the invention having a refractive surface that includes controlled surface modulations superimposed on a base profile.

FIG. 1 illustrates schematically an exemplary lens 10 according to the teachings of the invention that includes a lens optic 12 having two refractive surfaces 14 and 16. Although the refractive surfaces are depicted as being generally convex, either surface can have a generally concave shape. Alternatively, the surfaces 14 and 16 can be selected to generate a plano-concave or a plano-convex lens. Hence, a lens according to the teachings of the invention can have positive or negative nominal power.

The lens optic 12 can be formed from a variety of biocompatible soft materials. For example, the lens optic 12 can be formed of a soft acrylic material, e.g., a copolymer of acrylate and methacrylate, or of hydrogel or silicone. Those having ordinary skill in the art will appreciate that in fact any soft biocompatible material that exhibits a requisite index of refraction for a particular application of the lens can be employed for generating a lens of the invention, such as the above exemplary lens 10.

The refractive surface 16 exhibits an undulating topography. For purposes of illustration, the surface modulations have been exaggerated. More specifically, the refractive surface 16 can be characterized by a base curvature or profile 18, depicted by the dashed lines, on which a continuous pattern 20 of surface deviations are superimposed. The exemplary base profile 18 is generally spherical and is radially symmetric about an optical axis 22 of the lens body 12. Similarly, in this exemplary embodiment, the continuous pattern of surface deviations is also radially symmetric about the optical axis 22. Although the base profile 18 in this embodiment is spherical, in other embodiments, aspherical base profiles can be utilized in the practice of the invention.

Figure 2:
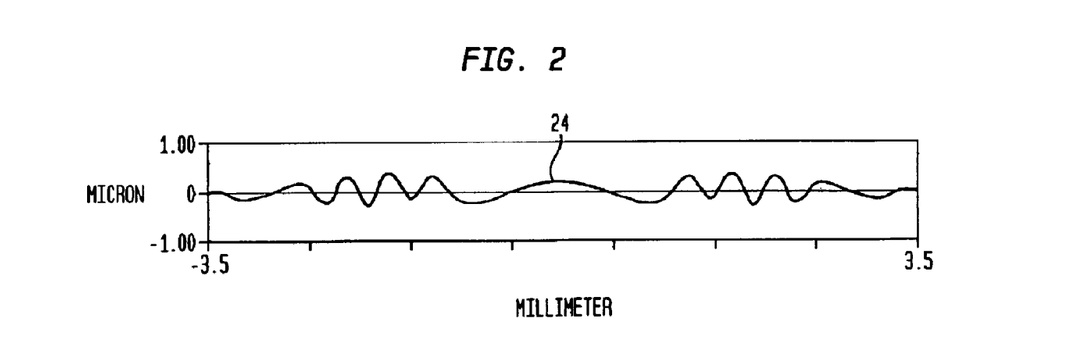
FIG. 2 illustrates a one-dimensional continuous curve corresponding to the pattern of surface deviations of the undulating refractive surface of the lens of FIG. 1 after subtracting the base curve.

FIG. 2 illustrates a one-dimensional continuous curve 24 corresponding to the pattern of deviations 20 from the base profile of lens 10 (FIG. 1) at each radial position about a central point 26 corresponding to an intersection of the optical axis 22 with the refractive surface 16. In other words, the one-dimensional curve 24 indicates a radial profile obtained by subtracting the base profile from the undulating topography of the surface 16 in order to more clearly depict the surface deviations. The curve 24 illustrates that the surface deviations can be characterized by a sinusoidal type continuous function, and that the surface deviations exhibit peak-to-valley excursions about the underlying base profile in a range of about −0.5 to about 0.5 microns.

The above surface deviations, although small, are effective in spreading out the focal depth of the lens. Without being limited to any particular theory, the effect of the controlled modulations of the topography of the refractive surface 16 in enhancing the depth of field of the lens can be understood by considering the local slope variations of the surface 16. More particularly, while some portions of the undulating surface 16 are parallel to the underlying spherical base curvature 18, some other portions are either steeper or flatter than the corresponding portions of the underlying curvature. Hence, while the parallel portions can direct an incident light beam to a nominal focal plane of the lens, or in proximity thereof, the steeper and the flatter portions direct incident light beams slightly in front of or slightly beyond the nominal focal plane. As described in more detail below, these beams cooperatively generate a single image that exhibits an acceptable level of contrast over a range of defocus distances. In this manner, the depth of field of the lens is enhanced by at least about 40%, and more preferably by at least about 50%, relative to a similar lens that is devoid of the surface deviations while ensuring that the contrast of the image remains within an acceptable range.

As known to those having ordinary skill in the art, a quantitative measure of image contrast provided by a lens can be obtained by measuring and/or calculating a Modulation Transfer Function (MTF) associated with the lens. The MTF can be employed as a primary measure of optical performance of a lens that allows comparison among different lenses. In general, a contrast or modulation associated with an optical signal, e.g., a two-dimensional sinusoidal pattern of light intensity distribution emanated or reflected by an object to be imaged or associated with the image of such an object, can be defined in accordance with the following relation:

$$\frac{I_{max} - I_{min}}{I_{max} + I_{min}}$$

wherein $I_{max}$ and $I_{min}$ indicate, respectively, a maximum or a minimum intensity associated with the signal. Such a contrast can be obtained for each spatial frequency present in the optical signal. An MTF of an imaging optical system, such as a lens, can then be defined as a ratio of a contrast associated with an image of an object formed by the optical system relative to a contrast associated with the object.

The MTF associated with a lens is not only dependent on spatial frequencies of the intensity distribution of the light illuminating the lens, but it can also be affected by other factors, such as, the size of an aperture employed, and the wavelength of the illuminating light. Hence, a depth of field of a lens as used herein is defined, as also described above, as an amount of defocus associated with the lens at which a through-focus MTF measured with a 3 mm aperture and green light exhibits a value of at least about 0.15 (15%) at a spatial frequency equal to about one-third of the cut-off spatial frequency for the measurement conditions. The MTF values are herein reported interchangeably as fractional numbers or as percentages, as is well understood in the art.

The cut-off spatial frequency is given by:

$$f_{diff} = \frac{n \times a}{\lambda \times d} \qquad \text{Eq. (1)}$$

wherein $f_{diff}$ denotes the cut-off spatial frequency, herein also referred to as the diffraction limited spatial frequency, n denotes the refractive index of a medium in which an image is formed by the lens, a denotes the aperture (e.g., pupil) diameter, and d denotes a distance from the lens to the image, and $\lambda$ denotes the wavelength of light illuminating the lens.

A lens according to the teachings of invention, such as the above exemplary lens 10, can exhibit a through-focus transfer function indicating a contrast level of at least about 15% at spatial frequencies less than or equal to about one-third of a diffraction limited spatial frequency associated with the lens.

The modulation transfer function of a lens of the invention can be measured, for example, in a simple wet cell, in a model eye or in air. The data presented below regarding the MTF of various exemplary lenses of the invention was obtained in air by utilizing green light at a wavelength of about 550 nm and standard measurement techniques. A variety of commercially available systems can be employed for such MTF measurements. For example, measurement instruments marketed by Image Science of Oxford, U.K. can be utilized.

A variety of patterns of surface deviations according to the invention can be applied to a base profile of a refractive surface of a lens according to the teachings of the invention in order to enhance its depth of field. One class of such surface deviations, which are radially symmetric about an optical axis of the lens, can be characterized by a one-dimensional modulation function in accordance with the following relation:

$$Z(r) = A(r)\cos(B(r)r^2) \qquad \text{Eq. (2)}$$

wherein $Z(r)$ denotes a surface deviation associated with the refractive surface at a radial distance r from an optical axis of the lens, and $A(r)$ and $B(r)$ are functions of radial distance r. The functions A and B are selected so as to enhance a depth of field of the lens by at least about 40%, and more preferably by at least about 50%, relative to a lens having the same lens body and the refractive surface, but without the surface deviations.

In many preferred embodiments, the parameter A is selected to have a maximum value in a range of about 0.15 microns to about 0.45 microns, and the parameter B is selected to have a minimum value in a range of about $$\frac{2\pi}{5}$$

(microns)$^{-2}$ to about $2\pi$(microns)$^{-2}$. More generally, the parameter A is selected to have a maximum value in a range of about $$\frac{1}{100*(n_2-n_1)}$$

to about $$\frac{1}{10*(n_2-n_1)}$$

microns, wherein $n_2$ denotes an index of refraction of the lens body and $n_1$ denotes an index of refraction of an environment in which the lens is disposed.

In some embodiments, the surface deviations applied to a refractive surface of the lens are defined in accordance with the above Equation (2) in which the functional parameters A and B are constants, and hence do not vary with radial distance from an optical axis of the lens. For example, the surface deviations can be defined in accordance with the following equation:

$$Z(r) = 0.22\cos\left(\frac{2\pi r^2}{2.2}\right) \qquad \text{Eq. (3)}$$

wherein the A parameter is selected to be 0.22 microns, and the B parameter is selected to be $$\frac{2\pi}{2.2}$$

(microns)$^{-2}$.

Figure 3:
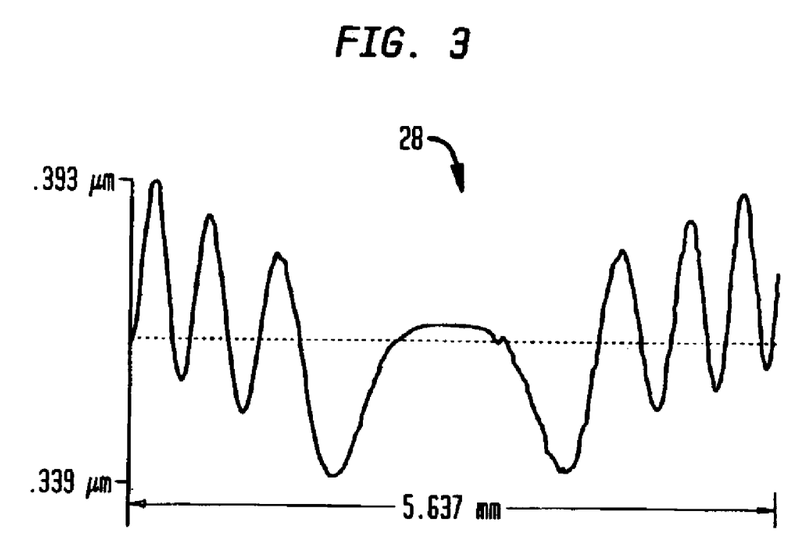
FIG. 3 is a graph indicative of surface topograply of a refractive surface of a lens formed according to the teachings of the invention versus distance from an optical axis of the lens, illustrating a sinusoidal-type continuously varying profile.

FIG. 3 illustrates a sinusoidal type continuously varying curve 28 depicting the profile of a surface of a lens of the invention having surface deviations from a base profile in accordance with the above Equation (3). The curve 28 illustrates that the surface deviations exhibit a height at each radial position, that is, a displacement from a base profile at each radial position in a direction perpendicular to the radial direction, in a range of ±0.22 microns. Further, the dependence of the cosine function on the square of the radial distance from an optical axis of the lens results in higher modulation frequencies as the radial distance from the optical axis increases.

In other embodiments, each of the A and B parameters in the above Equation (2) can be chosen to have a selected dependence on the radial distance (r) from an optical axis of the lens. For example, either A or B, or both, can be in the form of a polynomial of rank n defined in accordance with the following relations:

$$A(r) = a + a_1 r + a_2 r^2 + \ldots + a_n r^n \qquad \text{Eq. (4).}$$

$$B(r) = b_0 + b_1 r + b_2 r^2 + \ldots + b_n r^n \qquad \text{Eq. (5).}$$

wherein n is less than or equal to 20, and preferably less than or equal to 10, and r denotes a radial distance from an optical axis of the lens. The parameters $a_0$–$a_n$ and $b_0$–$b_n$ are selected such that the pattern of surface deviations generated by utilizing these parameters would enhance the depth of field of the lens by at least about 40%, and more preferably by at least about 50%, relative to a similar lens that lacks the surface deviations.

The above parameters $a_0$–$a_n$ and $b_0$–$b_n$ can be selected and optimized, for each rank of the above polynominals characterized by Equations (4) and (5), experimentally or theoretically, or both. For example, a ray tracing program, such as OSLO, marketed by Lambda Research Corporation of Littleton, Mass., U.S.A, can be employed to model the focusing performance of a refractive surface of a lens exhibiting a pattern of surface deviations, superimposed on a base profile, in accordance with a selected set of the $a_0$–$a_n$ and $b_0$–$b_n$ parameters. The parameters can be adjusted until a desired enhancement of the depth of field is achieved. Alternatively, model lenses exhibiting surface deviations based on different values of the $a_0$–$a_n$ and $b_0$–$b_n$ parameters can be manufactured. The focusing performance of such model lenses can be measured experimentally in order to find one or more parameter sets that would provide a desired enhancement of the depth of field of the lens.

A mixed theoretical and experimental approach can also be employed. For example, theoretical modeling, such as that described above, can be employed to narrow down the range of possible values for the parameters, and experimental techniques can be utilized to select optimal values for the parameters from the range of values indicated by theoretical modeling. Those having ordinary skill in the art will appreciate that various variations of the above methods can be employed to obtain suitable values of the parameters for any particular application of the lens.

Figure 4A:
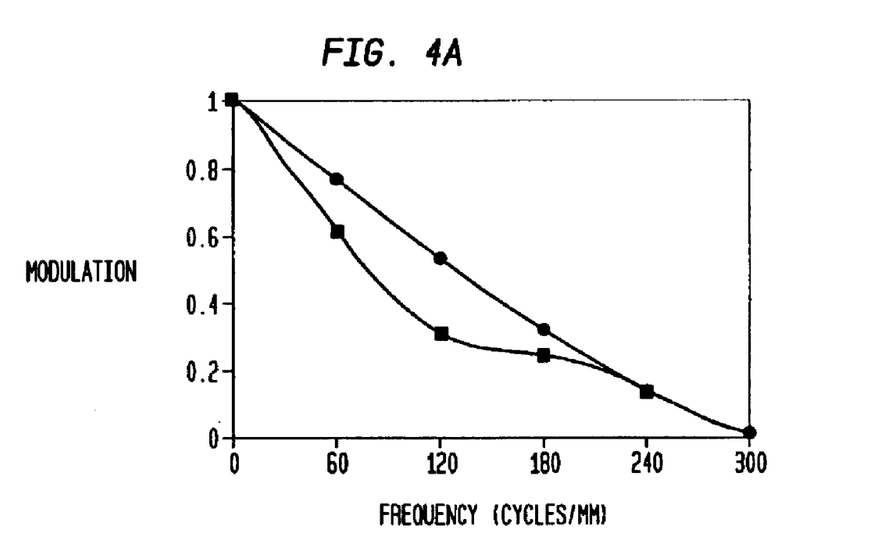
FIG. 4A is a graph of a calculated monochromatic MTF versus spatial frequency for a control lens.
Figure 4B:
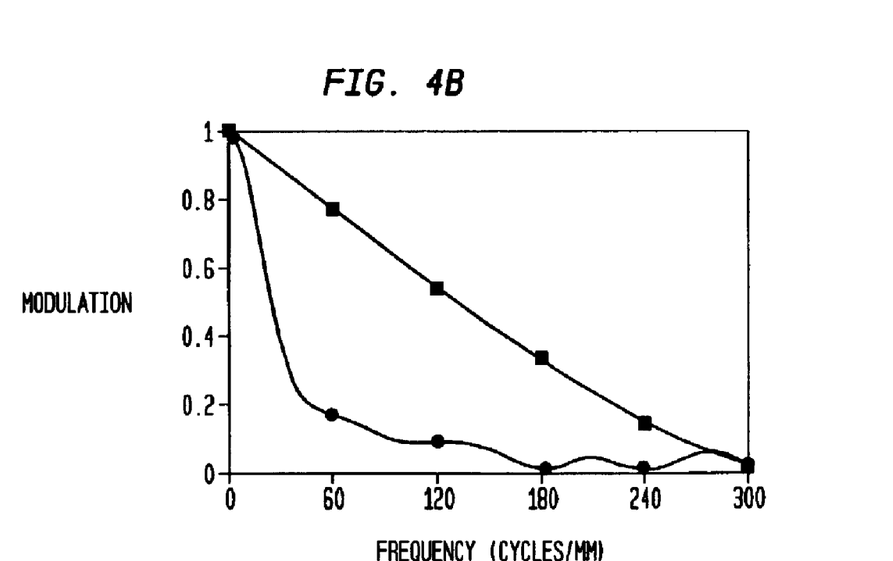
FIG. 4B is a graph of a calculated monochromatic MTF versus spatial frequency for a lens according to the teachings of invention having the same design as the control lens of FIG. 4A but with surface modulations.

By way of example only, and to further illustrate the efficacy of the methods of the invention for generating an ophthalmic lens having an enhanced depth of field, theoretically and experimentally measured focusing performance of a prototype lens, formed of poly methyl methacrylate (PMMA) in accordance with the teachings of the invention, will be described below. The prototype lens was modeled so as to have a refractive surface with a spherical base profile on which a pattern of surface modulations, characterized by the above Equation (3), was superimposed. The undulating surface was inputted into an OSLO premium ray-tracing program, marketed by Lambda Research Corporation of Littleton, Mass., U.S.A, as an anterior surface of a PMMA lens in air. A monochromatic MTF, for illuminating light having a wavelength of 550 nm, was then calculated at best focus for a 3 mm diameter aperture for selected spatial frequencies. The spatial frequency range of interest for this lens in air is fairly similar to that for an IOL in the eye. A similar MTF was also calculated for a control lens having the same structure but lacking the surface modulations. The results of the calculations, performed for each lens alone in air with a 3 mm aperture, are presented in FIGS. 4A and 4B for the control lens and the prototype lens, respectively. The lower ⅓ of the spatial frequency range is comparable to the values experienced in the eye, with 20/20 vision corresponding approximately to 100 line pairs per mm.

Figure 5A:
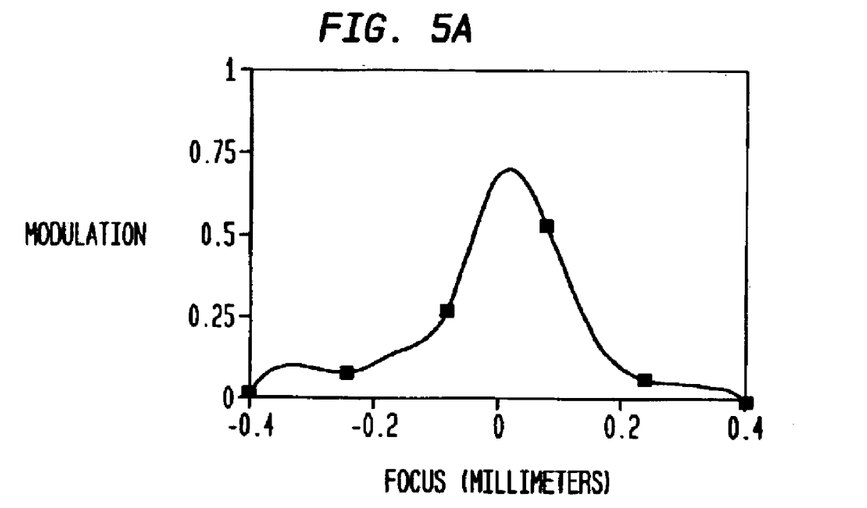
FIG. 5A is a graph of a calculated through-focus MTF at a spatial frequency of 50 cycles/mm, measured in air, as a function of defocus distance (in units of millimeters) for a control lens that is devoid of surface modulations according to the teachings of the invention.
Figure 5B:
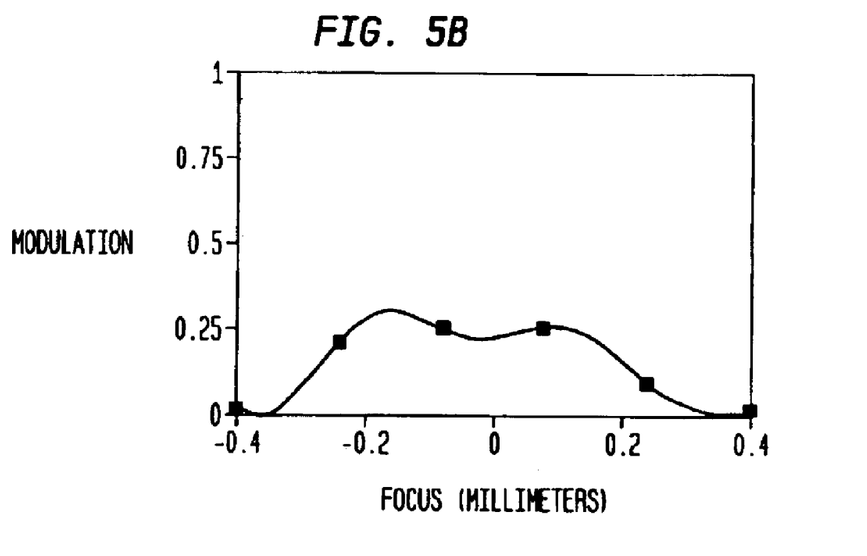
FIG. 5B is a graph of a calculated through-focus MTF at a spatial frequency of 50 cycles/mm, measured in air, as a function of defocus distance (in units of millimeters) for a lens having the structure of the control lens of FIG. 5A and further including a refractive surface having surface modulations in accordance with the teachings of the invention.

Moreover, through-focus MTFs at 50 line pairs per millimeter for the control lens (FIG. 5A) and the prototype lens having sinusoidal surface variations (FIG. 5B) were calculated for a range of defocus distances. Similar to the calculations presented in FIGS. 4A and 4B, these calculations are also based on each lens being alone in air and utilizing a 3 mm aperture. A comparison of FIG. 5A with FIG. 5B illustrates that although the maximum value of MTF for the prototype lens is lower than the corresponding value for the control lens, the prototype lens exhibits an enhanced depth of focus. For example, the MTF values associated with the prototype lens at defocus distances of −0.2 and 0.2 millimeters are approximately two times as high as the corresponding values for the control lens. In other words, although the exemplary prototype lens provides a generally reduced contrast, it improves the depth of field over a range of defocus distances while providing a contrast that is sufficient for resolving the image. In particular, the illustrated values of MTF for the prototype lens for defocus distances in a range of about −0.2 to about 0.2 millimeters are greater than about 15%.

In addition, a planar prototype lens having a refractive surface with continuously varying surface deviations characterized by the above Equation (3) was manufactured, and its focusing properties were measured, as discussed in detail below. The prototype lens was fabricated by utilizing a single point diamond turning lathe to apply the surface deviations to a surface of PMMA disk.

Figure 6:
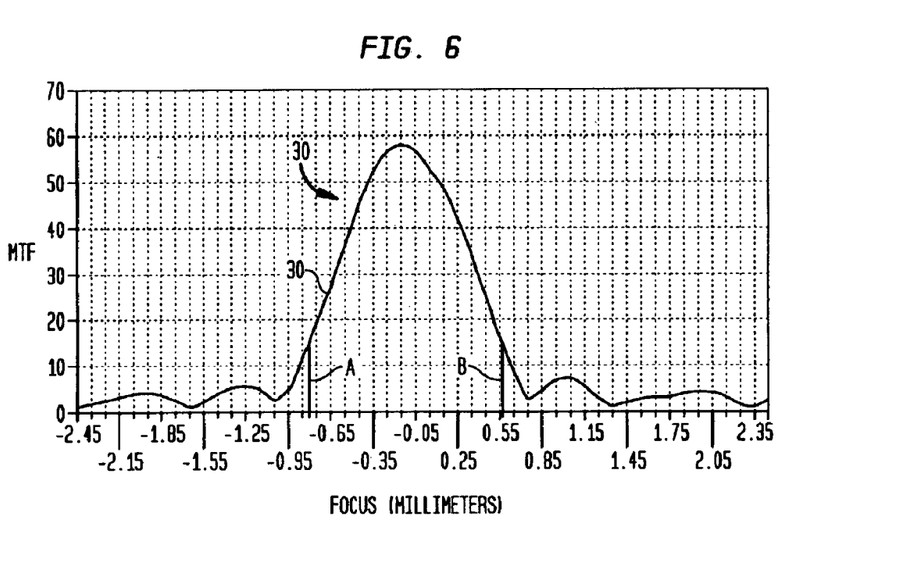
FIG. 6 is a graph of an experimental through-focus MTF at a spatial frequency of about 30 lp/mm versus defocus distance (in units of millimeters) of a fabricated control lens that is devoid of surface modulations according to the teachings of the invention.
Figure 7:
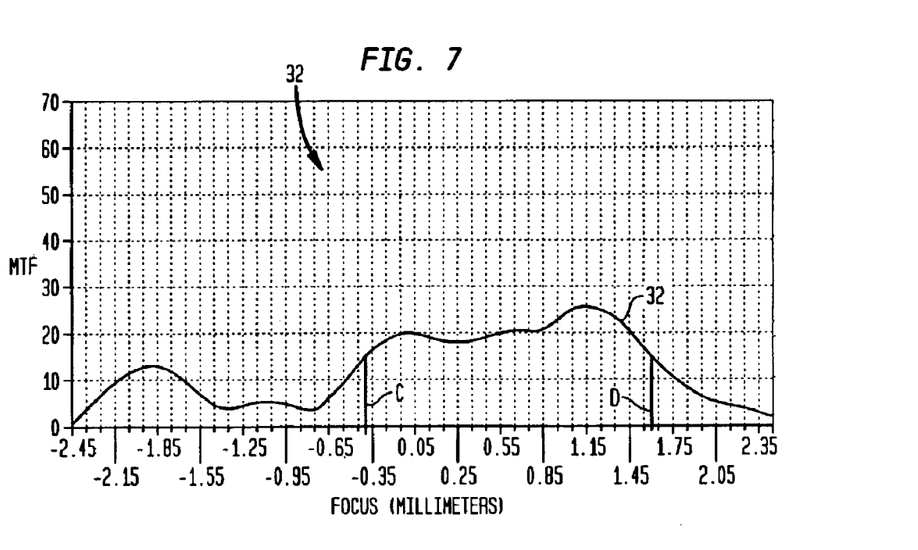
FIG. 7 is a graph of an experimental through-focus MTF at a spatial frequency of about 30 lp/mm of a fabricated prototype lens of the invention, having the structure of the control lens associated with FIG. 6 but with surface modulations, as a function of defocus distance (in units of millimeters) measured with a 3 mm aperture.

FIGS. 6 illustrates an experimentally measured through-focus modulation transfer function (MTF) 30 corresponding to a fabricated control lens having the same optic, a low power lens (nominally 0 D), as the above prototype lens but without the surface modulations according to the teachings of the invention. And FIG. 7 illustrates an experimentally measured MTF 32 corresponding to the above prototype lens. Each of the MTFs 30 and 32 was measured in air by placing the respective lens in front of a 50 mm focal length high quality lens and employing monochromatic illumination light at a wavelength of 550 nm with a 3 mm aperture, and utilizing standard measurement techniques. The presented through-focus MTFs correspond to about 30 lp/mm, or about ⅓ of a spatial frequency of 100 lp/mm for a 3 mm pupil, which is about ⅓ of that of an IOL in air. In these MTFs, a defocus distance of ±2.5 mm is equivalent to ±1 Diopter.

The through-focus MTF 32 of the fabricated prototype lens having surface modulations according to the teachings of the invention exhibits multiple peaks, or in other words, it exhibits a multi-focal behavior. The bars A/B and C/D superimposed on the MTFs 30 and 32 corresponding to the control lens and the prototype lens, respectively, delimit a range of defocus distance over which the MTF is greater than 15%. While this range of defocus, i.e., the range between the intercepts, for the control lens is about 0.57 Diopters, the corresponding range for the prototype lens is about 0.82 Diopters. That is, the prototype lens having a refractive surface with surface deviations in accordance with the teachings of the invention exhibits a much enhanced depth of field.

Figure 8A:
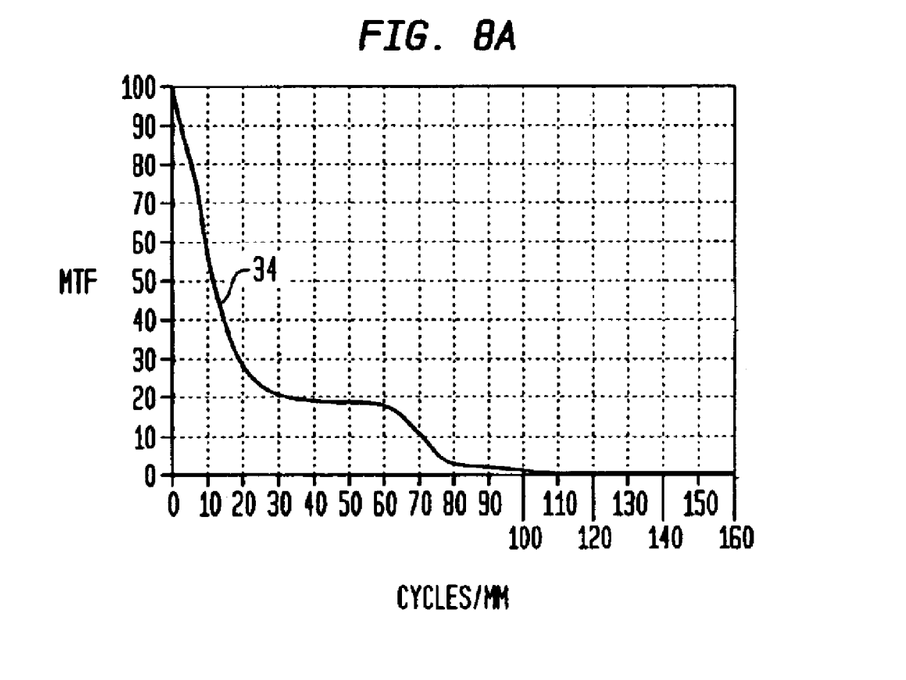
FIG. 8A is a graph of an in-focus MTF for a prototype lens formed according to the teachings of the invention versus a range of spatial frequencies.
Figure 8B:
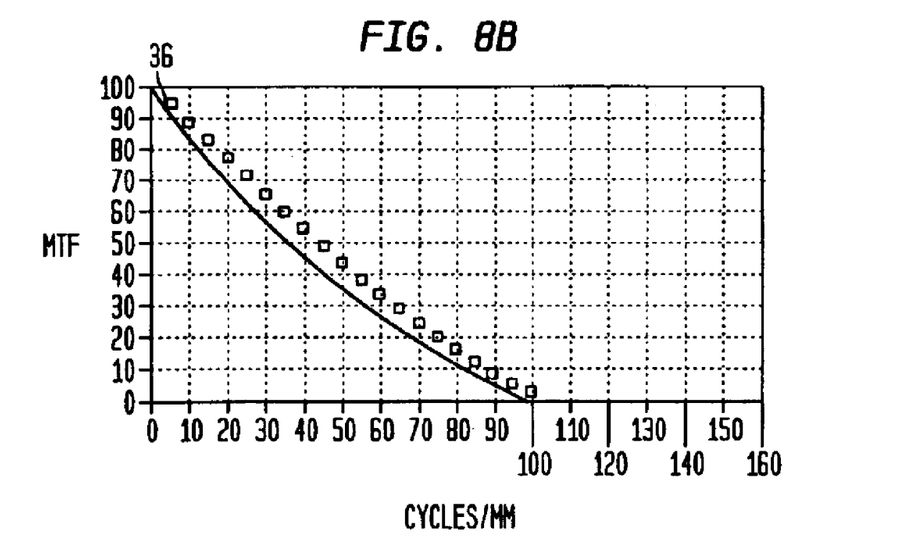
FIG. 8B is a graph of an in-focus MTF versus a range of spatial frequencies for a control lens having the structure of the prototype lens associated with FIG. 8A but without surface modulations according to the teachings of the invention.

In addition to through-focus MTF measurements, in-focus MTF measurements for a range of spatial frequencies were also obtained (e.g., by employing instruments marketed by Image Science of Oxford, U.K.) for both the fabricated prototype lens and the control lens by utilizing 3 mm aperture and monochromatic green light having a wavelength of 550 nm. The measurement conditions were generally the same as those described above in connection with FIGS. 6 and 7. FIG. 8A illustrates an in-focus MTF for the prototype lens described above having a refractive surface with sinusoidal type surface modulations in accordance with the above Equation (3) while FIG. 8B illustrates an in-focus MTF with the control lens that lacks the surface modulations.

A comparison of the depicted in-focus MTF of the fabricated prototype lens relative to that of the control lens indicates that the prototype lens exhibits a contrast at low spatial frequencies, e.g., spatial frequencies below about 20 lp/mm, decreases with increasing frequency more rapidly than the corresponding change exhibited by the control lens. The contrast of the prototype lens, however, flattens out at spatial frequencies in a range of about 30 to about 60 lp/mm, and shows a decrease beyond this range to vanishing values at a spatial frequency of approximately 110 lp/mm.

A pattern of continuous surface deviations in accordance with the teachings of the invention is not limited to one of the exemplary patterns described above. In fact, such a pattern of surface deviations can be characterized by a variety of continuous functional forms so long as the surface deviations would result in enhancing a depth of field of the lens by at least about 40 percent, and more preferably by at least about 50 percent. By way of example, in some embodiments of the invention, a refractive surface of a lens of the invention having a pattern of surface deviations can be defined recursively as a spline surface by employing a spline fitting procedure. For example, in such a spline surface construction method, at each of a plurality of locations at selected radial distances from an optical axis, a height, i.e., a distance perpendicular to radial direction, from a base profile, such as a radially symmetric spherical base profile, as well as a value of slope are defined. A spline fitting procedure is then utilized to define a continuously varying surface that extends through the defined locations and has the defined slopes at each location.

The focusing performance of a lens having such a modulated refractive surface can be determined either theoretically or experimentally, or both, and the deviated locations and/or their associated slopes can be iteratively adjusted so as to obtain a desired enhancement of the depth of field, e.g., an enhancement greater than about 50%. Further information regarding such a spline fitting procedure for constructing a refractive surface according to the teachings of the invention can be found in Example I below.

An ophthalmic lens according to the teachings of the invention can be employed in a variety of vision correction applications. Such applications include, but are not limited to, intraocular lenses (IOLs), contact lenses, instrastromal implants and other refractive devices. For example, a lens of the invention can be employed as an improved IOL that ameliorates residual refractive errors that are typically present after cataract surgery. It is well known in the practice of cataract surgery that factors, such as surgical instrument precision, IOL product precision, preoperative biometry data, surgeon's skill level and capsular bag differences among individuals, can cause variations in a desired refractive error after surgery. One standard deviation of such variations of the refractive error can be as large as 0.5 Diopters. Such residual refractive error, which can persist for a long time, can degrade the patient's visual acuity. Consequently, many patients require spectacles to achieve enhanced post-operative visual acuity.

An IOL formed in accordance with the teachings of the invention can be utilized to render outcomes of cataract surgery more predictable, thus reducing dependence on spectacles after cataract surgery. In particular, an IOL of the invention can include a refractive surface having surface deviations that cause an enhancement of the IOL's depth of field, and hence lower the IOL's sensitivity to errors described above. In other words, an eye of a patient in which an IOL of the invention is implanted exhibits an increased depth of focus, and hence provides improved visual performance within a wider range of defocus. Accordingly, post-operative variations in refractive error have a reduced impact on the patient's visual performance.

The above data presented for exemplary lenses formed according to the teachings of the invention indicate that these lenses exhibit improved depth of field when measured in air in which a typical IOL exhibits a limiting spatial frequency that happens to be substantially similar to that measured for the same lens in a model eye. To further illustrate the efficacy of lenses of the invention for improving depth of field when employed in patients, the results of visual performances of prototype lenses formed in accordance with the teachings of the invention obtained by employing five human subjects, are discussed below. A visual acuity of 20/40 was selected as a reference level that is indicative of acceptable good vision, although gradation of vision quality generally forms a continuous function. For these experiments, the depth of focus was defined as a range of defocus distances within which the visual acuity is 20/40 or better.

Prototype lenses with small positive focal powers (approximately +0.5 D) were manufactured by employing PMMA. All lenses were sized and shaped to fit into spectacles trial lens frames. Some of the prototype lenses included sinusodial-type variations of at least one refractive surface while others were devoid of such surface variations to be utilized as control lenses.

Five subjects with ages ranging from mid-twenties to mid-forties were enrolled in experimental study of the focusing performance of the prototype lenses formed according to the teachings of the invention. Only the right eyes of the subjects were utilized for visual tests. The best spectacle correction prescription for each eye was determined by an experienced optometrist.

All eyes in the experiment exhibited low or mild myopia, but were otherwise normal and healthy. The visual tests were performed in a standard optometry clinic by employing the B-VAT2 Snellen's visual acuity chart. The visual acuity chart was displayed on a monitor to each subject, by typically displaying three lines of letters with decreasing letter sizes. The letters were randomized in sequence by a control system.

The sphero-cylindrical refractive errors of the subjects were best corrected by trial lenses. The visual tests were conducted under room lighting conditions to simulate the normal viewing condition in daily life. No drug was used to dilate the pupil and paralyze accommodation. In order to control the accommodation impact in experimental design, the positive defocus was introduced to the eyes under test by placing the positive trial lens in front of the eye. Such positive defocus would largely prevent accommodation because accommodation cannot overcome positive defocus error.

The subject was allowed to make guesses about those letters that the subject was not able to readily resolve. The visual acuity was recorded as a two-component indicator. The main component was selected to be the line with the smallest letters that the subject could read, and the fraction component was selected to be the cumulative number error made by the subject in reading the letters. The main and fraction components of the visual acuity indicator were utilized to calculate the minimum angle of resolution (MAR) in units of arcmin. The larger the minimum angle of resolution, the worse is the visual acuity. For example, 1 MAR corresponds to 20/20 vision. The MAR can be plotted as a function of defocus distance for illustrating the focusing performance of a trial lens.

Although the visual performance results vary from one subject to another, a statistical analysis of the data indicated that the prototype lenses of the invention having sinusoidal variations of surface topography provide, on average, an enhancement of depth of field of approximately 0.78 D.

Figure 9:
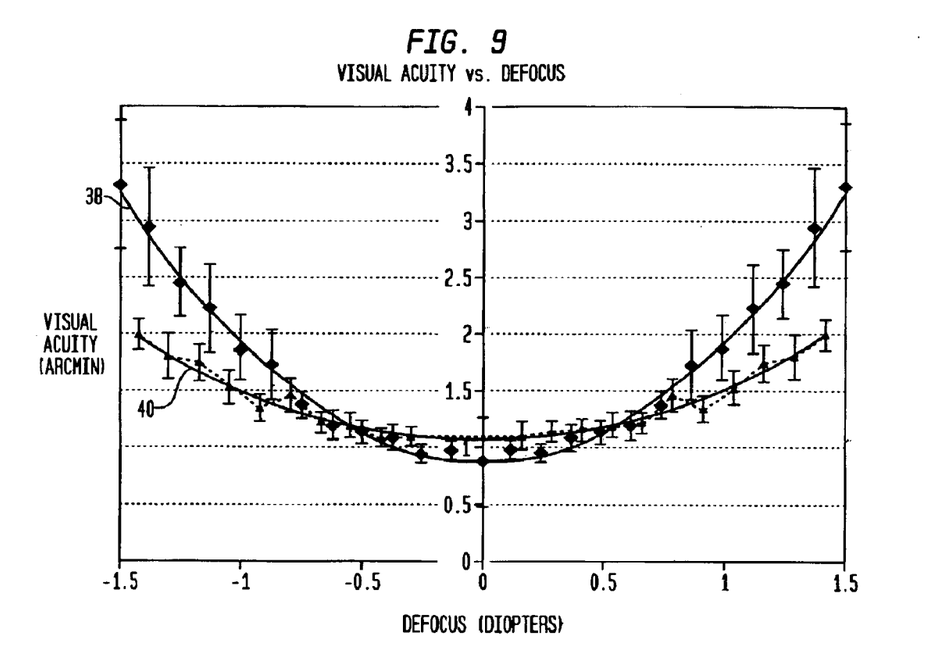
FIG. 9 presents two graphs for comparison of visual acuity data corresponding to a lens of the invention with that of a control lens compiled by averaging the respective visual acuity data obtained from five human subjects.

More particularly, FIG. 9 illustrates curves 38 and 40 that represent the average visual acuity data for the control lenses and the prototype lenses, respectively, utilized in the above visual acuity tests. In the curves 38 and 40, the visual acuity data for negative defocus distances was obtained by flipping the measured visual acuity data for positive defocus distances relative to the origin. The curve 40 is generally flatter than the control curve 38, thus signifying that the lenses of the invention exhibit an enhanced depth of focus. In other words, over a wide range of defocus distances, for a given value of visual acuity, a lens of the invention exhibits a larger defocus distance.

The ophthalmic lenses of the invention can be employed in a variety of vision correction applications, such as IOLs, contact lenses and intrastromal implants to provide an enhanced depth of field. In other words, the use of a lens of the invention can increase the range of defocus over which an acceptable visual acuity is obtained. For example, in the case of cataract surgery, 95% of the patients can have a post-operative refractive error of 1 D or less. In the absence of utilizing a lens of the invention, a 1 D defocus can degrade the patient's visual acuity, for example, from 20/18 to 20/40. In contrast, the use of a lens of the invention can result in a much reduced change in visual acuity for the same refractive error, for example, from 20/22 to 20/30.

As discussed above, the surface variations of a refractive lens of the invention can have a variety of functional forms so long as they are continuous across the lens surface, and provide a desired depth of focus. Example I below provides an exemplary method for modeling a lens surface according to the teachings of the invention by employing a spline fitting procedure.

EXAMPLE I

Figure 10:
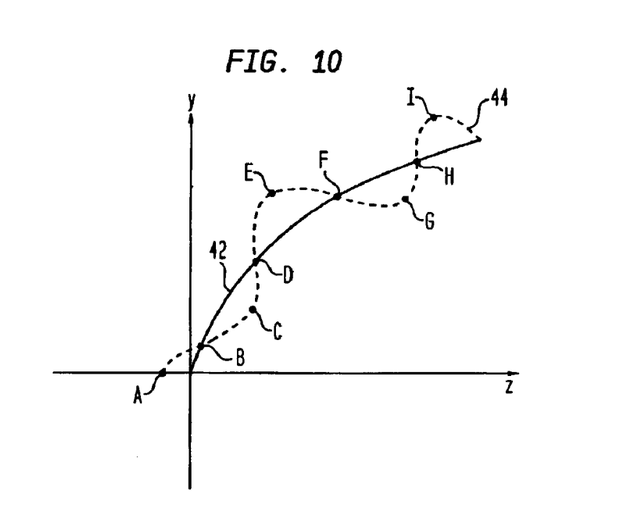
FIG. 10 presents a graph for describing a spline fitting procedure for modeling a refractive surface having controlled modulations according to the teachings of the invention.

One exemplary method for modeling a refractive lens of the invention having surface deviations from a base profile in which a spline fitting procedure is employed is described below. With reference to FIG. 10, a solid curve 42 represents a base profile of such a refractive surface, which is selected in this example to be spherical. The z-axis is selected to be the optical axis of the lens such as the base profile is symmetric about the z-axis. Hence, only the upper portion of the surface, i.e., positive y direction, is considered with the understanding that the variations in the negative y directions mirror those in the positive y direction.

A plurality of exemplary off-axis locations A, B, C, D, E, F, G, H, and I each having selected z-axis coordinate and offset from the base profile, are chosen. An initial value of slope is assigned to each of these locations. A spline fitting procedure is employed to form an initial surface, e.g., dashed surface 44, that passes through these locations and exhibits, at each location, the respective value of the slope. Each of the locations B, D, F, and H corresponds to a crossing of the dashed surface 44 with the base profile while each of the locations A, C, E, G, and I corresponds to a maximum deviation of the dashed surface from the base profile in a region between two consecutive crossings. A merit function that is indicative of a depth of field achievable by utilizing the surface passing through the locations, e.g., a modulation transfer function, is calculated, e.g., by ray-tracing or otherwise, for this surface. The values of the slopes, and hence the shape of the surface 44, are iteratively adjusted until an optimal value of the merit function is achieved, thereby producing a model refractive surface exhibiting desired controlled surface modulations. In some embodiments, in addition to the slopes, the deviations of the locations A, C, E, G, and I relative to the base profile, i.e., surface 42, can also be allowed to vary, and iteratively adjusted, until an optimal value of the merit function is obtained.

Those having ordinary skill in the art will appreciate that various modifications can be made to the above embodiments without departing from the scope of the invention.

What is claimed is:

1. A monofocal ophthalmic lens having an extended depth of field, comprising
    a lens optic providing a nominal diopter power and further characterized by at least one refractive surface having a base curvature, and
    a pattern of surface deviations superimposed on said base curvature so as to modulate the topography of said refractive surface in a range of about −0.5 microns to about 0.5 microns so as to enhance a depth of field of said lens by at least about 40% relative to a lens having said lens optic and said refractive surface without said surface deviations.

2. The monofocal lens of claim 1, wherein a through-focus modulation transfer function of said lens indicates an MTF contrast level of at least about 0.15 at spatial frequencies less than or equal to about one-third of a diffraction limited spatial frequency associated with said lens.

3. The monofocal lens of claim 1, wherein said pattern of surface deviations is characterized by a continuously varying current.

4. The monofocal lens of claim 3, wherein said pattern of surface deviations is characterized by a sinusoidal type curve.

5. The monofocal lens of claim 3, wherein said base curvature is radially symmetric.

6. The monofocal lens of claim 5, wherein said pattern of surface deviations is radially symmetric.

7. A monofocal ophthalmic lens for vision correction having an extended depth of field, comprising
    a lens optic comprising a refractive surface having a base profile modulated by a pattern of surface deviations in accordance with the relation:

$$Z(r)=A(r)\cos(B(r)r^2)$$

wherein Z(r) denotes a surface deviation at a radial distance r from an optical axis of said lens, and A(r) and B(r) are functions of radial distance r selected so as to enhance a depth of field of said lens by at least 50% relative to a lens having said lens body and said refractive surface without said surface deviations.

8. The monofocal lens of claim 7, wherein A is selected to have a maximum value in a range of about 0.05 microns to about 0.5 microns.

9. The monofocal lens of claim 8, wherein A is selected to have a maximum value in a range of about 0.15 microns to about 0.45 microns.

10. The monofocal lens of claim 8, wherein B is selected to have a minimum value in a range of about $$\frac{2\pi}{5}$$

to about $2\pi$.

11. The monofocal lens of claim 7, wherein A is selected to have a maximum value in a range of about $$\frac{1}{100*(n_2-n_1)}$$

to about $$\frac{1}{10*(n_2-n_1)}$$

microns, wherein $n_2$ denotes an index of refraction of said lens body and $n_1$ denotes an index of refraction of an environment in which the lens is disposed.

12. The monofocal lens of claim 8, wherein A(r) and B(r) are defined as polynomials in accordance with the relations:

$$A(r)=a_0+a_1r+a_2r^2+\ldots+a_nr^n$$

$$B(r)=b_0+b_1r+b_2r^2+\ldots+b_nr^n$$

wherein n is selected to be less than about 20, and parameters $a_0$–$a_n$ and $b_0$–$b_n$ are selected so as to provide said enhanced depth of field.

13. The monofocal lens of claim 1, wherein said lens body is formed of a biocompatible soft material.

14. The monofocal lens of claim 1, wherein said lens body is formed of any of hydrogel, silicone or a soft acrylic material.

15. The monofocal lens of claim 1, wherein said lens body is formed of a copolymer of acrylate and methacrylate.

16. The monofocal lens of claim 1, wherein said lens provides nominal focal power in a range of about 20 to about 22 Diopters.

17. A method for generating an intraocular lens for vision correction having an extended depth of field, comprising
    selecting a circularly symmetric base profile for at least a refractive surface of said lens,
    defining a circularly symmetric continuously varying pattern of surface deviations from said base profile, and
    applying said pattern of surface deviations to said base profile to define a continuously varying topography for said refractive surface,
    wherein said pattern of surface deviations is defined so as to enhance a depth of field of said lens by at least about 50% relative to a lens having a refractive lens with said base profile without said surface deviations.

18. The method of claim 17, wherein the step of defining the pattern of surface deviations from the base profile further comprises
    selecting a plurality of locations on said base profile each at a selected radial distance from an optical axis of said lens,
    for each of said locations, defining a position deviated from said location in a direction perpendicular to a radial direction and further defining a slope at said deviated position,
    utilizing a spline fitting procedure to define a continuously varying surface extending through said deviated positions and having said defined slopes at each of said deviated positions,
    determining an enhancement of a depth of field of said lens provided by employing said continuously varying surface as a profile of said refractive surface, and
    adjusting iteratively one or more of said deviated positions and/or said slopes at said deviated positions such that the enhancement of the depth of field is at least about 50%, thereby determining an optimal pattern of surface deviations.

* * * * *